US011328223B2

(12) United States Patent
Aso

(10) Patent No.: US 11,328,223 B2
(45) Date of Patent: May 10, 2022

(54) INFORMATION PROCESSING METHOD AND INFORMATION PROCESSING SYSTEM

(71) Applicant: Panasonic Intellectual Property Corporation of America, Torrance, CA (US)

(72) Inventor: Mitsuhiro Aso, Osaka (JP)

(73) Assignee: PANASONIC INTELLECTUAL PROPERTY CORPORATION OF AMERICA, Torrance, CA (US)

(*) Notice: Subject to any disclaimer, the term of this patent is extended or adjusted under 35 U.S.C. 154(b) by 0 days.

(21) Appl. No.: 16/933,326

(22) Filed: Jul. 20, 2020

(65) Prior Publication Data

US 2021/0027198 A1  Jan. 28, 2021

Related U.S. Application Data

(60) Provisional application No. 62/876,872, filed on Jul. 22, 2019.

(30) Foreign Application Priority Data

Nov. 8, 2019  (JP) .............................. JP2019-203483

(51) Int. Cl.
*G06N 20/00* (2019.01)
*G06F 3/0482* (2013.01)
*G06F 3/0488* (2022.01)
*G06F 3/04883* (2022.01)
*G06F 3/16* (2006.01)

(52) U.S. Cl.
CPC ........... *G06N 20/00* (2019.01); *G06F 3/0482* (2013.01); *G06F 3/0488* (2013.01); *G06F 3/04883* (2013.01); *G06F 3/167* (2013.01)

(58) Field of Classification Search
None
See application file for complete search history.

(56) References Cited

U.S. PATENT DOCUMENTS

| | | | |
|---|---|---|---|
| 2003/0004983 A1* | 1/2003 | Cohen | G06F 3/0489 715/205 |
| 2010/0194703 A1* | 8/2010 | Fedor | G06Q 30/02 715/810 |
| 2011/0004821 A1 | 1/2011 | Miyazawa et al. | |
| 2014/0201671 A1* | 7/2014 | Zhai | G06F 40/263 715/773 |
| 2014/0279739 A1* | 9/2014 | Elkington | G06N 20/00 706/12 |

(Continued)

FOREIGN PATENT DOCUMENTS

| | | |
|---|---|---|
| JP | 2011-13980 | 1/2011 |
| JP | 2017-215687 | 12/2017 |

*Primary Examiner* — Ryan Barrett
(74) *Attorney, Agent, or Firm* — Wenderoth, Lind & Ponack, L.L.P.

(57) ABSTRACT

An information processing method includes the processes of: obtaining food and drink data and presenting the food and drink data via a presentation device; generating options for the food and drink data, and presenting the options via the presentation device; generating selection reasons according to an option selected from among the options, and presenting the selection reasons via the presentation device; and controlling training of a machine learning model, in which the food and drink data is used, according to a result of an input in response to the selection reasons.

17 Claims, 12 Drawing Sheets

(56) References Cited

U.S. PATENT DOCUMENTS

| | | | |
|---|---|---|---|
| 2015/0189410 A1* | 7/2015 | Oh | H04R 3/00 |
| | | | 381/110 |
| 2016/0048282 A1* | 2/2016 | Bailiang | G06F 3/0481 |
| | | | 715/784 |
| 2016/0063993 A1* | 3/2016 | Dolan | G06F 16/00 |
| | | | 704/254 |
| 2018/0046470 A1* | 2/2018 | de Oliveira | G06F 3/0482 |
| 2018/0329551 A1* | 11/2018 | Feldman | G06F 3/041 |
| 2018/0364887 A1* | 12/2018 | Bell | H04L 67/18 |
| 2020/0026397 A1* | 1/2020 | Wohlstadter | G16C 20/10 |
| 2020/0387245 A1* | 12/2020 | Chen | G06F 3/03547 |
| 2021/0049674 A1* | 2/2021 | Periyathambi | G06N 20/00 |

* cited by examiner

INFORMATION PROCESSING METHOD AND INFORMATION PROCESSING SYSTEM

CROSS REFERENCE TO RELATED APPLICATIONS

The present application is based on and claims priority of Japanese Patent Application No. 2019-203483 filed on Nov. 8, 2019, and priority of U.S. Provisional Patent Application No. 62/876,872 filed on Jul. 22, 2019. The entire disclosures of the above-identified applications, including the specification, drawings and claims are incorporated herein by reference in its entirety.

FIELD

The present disclosure relates to an information processing method and an information processing system which control training of a machine learning model, in which food and drink data is used.

BACKGROUND

A recipe providing system has been disclosed which determines an attribute for identifying a preference of a user regarding cooking, collects information on the preference of the user regarding cooking that is identified by the attribute, and provides a recipe suitable to the preference of the user, based on the determined attribute of the user and the collected information on the preference of the user regarding cooking (Patent Literature (PTL) 1, for example).

CITATION LIST

Patent Literature

PTL 1: Japanese Unexamined Patent Application Publication No. 2017-215687

SUMMARY

Technical Problem

PTL 1 discloses that a preference is learned based on user's impression of a proposed recipe. However, there are instances where the user's impression is ambiguous because it varies according to the current weather, the user's physical condition, mood, schedule, etc. For that reason, there is a possibility that data that should not be learned is also used for the machine learning, making the learning ineffective.

In view of the above-described circumstances, one non-limiting and exemplary embodiment of the present disclosure provides an information processing method and the like capable of efficiently performing training of a machine learning model, in which food and drink data is used.

Solution to Problem

In one general aspect, the techniques disclosed in the present disclosure feature an information processing method including the processes of: obtaining food and drink data and presenting the food and drink data via a presentation device; generating options for the food and drink data, and presenting the options via the presentation device; generating selection reasons according to an option selected from among the options, and presenting the selection reasons via the presentation device; and controlling training of a machine learning model according to a result of an input in response to the selection reasons, the training using the food and drink data.

General and specific aspects disclosed above may be implemented using a system, a method, an integrated circuit, a computer program, or a computer-readable recording medium such as a compact disc-read only memory (CD-ROM), or any combination of systems, methods, integrated circuits, computer programs, or computer-readable recording media.

Additional benefits and advantages of the disclosed embodiments will be apparent from the Specification and Drawings. The benefits and/or advantages may be individually obtained by the various embodiments and features of the Specification and Drawings, which need not all be provided in order to obtain one or more of such benefits and/or advantages.

Advantageous Effects

With the information processing method and the like according to one or more exemplary embodiments or features disclosed herein provide an advantageous effect of efficiently performing training of a machine learning model, in which food and drink data is used.

BRIEF DESCRIPTION OF DRAWINGS

These and other advantages and features will become apparent from the following description thereof taken in conjunction with the accompanying Drawings, by way of non-limiting examples of embodiments disclosed herein.

FIG. 2A is a flowchart illustrating one example of the operation performed by the server according to the embodiment when the server transmits food and drink data and the like.

FIG. 2B is a flowchart illustrating another example of the operation performed by the server according to the embodiment when the server transmits food and drink data and the like.

FIG. 6A is a flowchart illustrating one example of the operation performed by a server according to a variation of the embodiment when the server transmits food and drink data and the like.

FIG. 6B is a flowchart illustrating another example of the operation performed by the server according to the variation of the embodiment when the server transmits food and drink data and the like.

Figure 1:
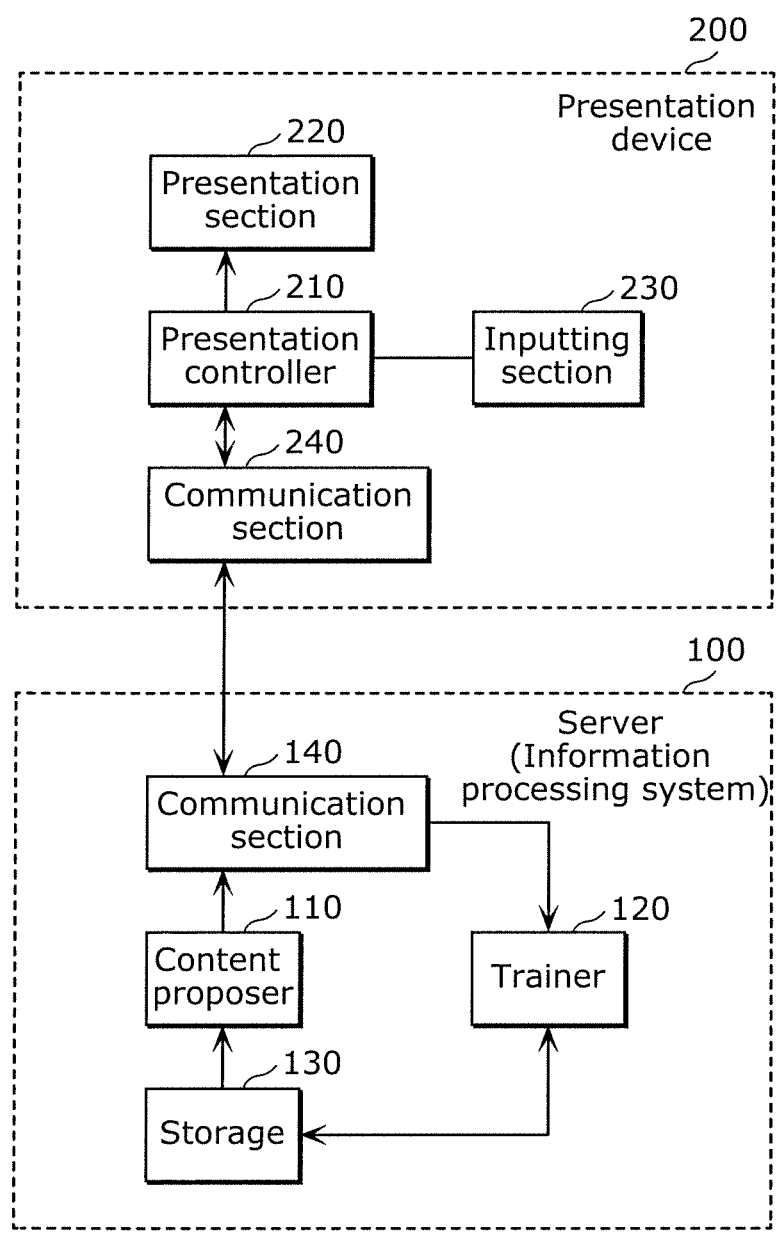
FIG. 1 is a block diagram illustrating one example of a server and a presentation device according to one exemplary embodiment.

DESCRIPTION OF EMBODIMENT (Underlying Knowledge Forming Basis of the Present Disclosure)

These general and specific aspects may be implemented using a system, a method, an integrated circuit, a computer program, or a computer-readable recording medium such as a CD-ROM, or any combination of systems, methods, integrated circuits, computer programs, or computer-readable recording media.

Hereinafter, certain exemplary embodiments are described in greater detail with reference to the accompanying Drawings.

Each of the exemplary embodiments described below shows a general or specific example. The numerical values, shapes, materials, elements, the arrangement and connection of the elements, steps, the processing order of the steps etc. shown in the following exemplary embodiments are mere examples, and therefore do not limit the scope of the appended Claims and their equivalents. Therefore, among the elements in the following exemplary embodiments, those not recited in any one of the independent claims are described as optional elements.

An information processing method according to one aspect of the present disclosure includes: obtaining food and drink data and presenting the food and drink data via a presentation device; generating options for the food and drink data, and presenting the options via the presentation device; generating selection reasons according to an option selected from among the options, and presenting the selection reasons via the presentation device; and controlling training of a machine learning model according to a result of an input in response to the selection reasons, the training using the food and drink data.

For example, there are instances where the user's impression of the food and drink data is ambiguous because it varies according to the current weather, the user's physical condition, mood, schedule, and the like. Accordingly, there is a possibility that such ambiguous impression may be data with low learning efficiency for the machine learning model for which the food and drink data is used. In view of the above-described circumstances, selection reasons (specifically, a plurality of selection reason candidates) are generated in accordance with the options for the food and drink data, and the generated selection reasons are presented on the presentation device to cause the user to input a selection reason selected from among the presented selection reasons. An input result in response to the selection reasons is adopted by the user not based on the impression that the user may come up with from moment to moment but from the selection reasons generated in detail and presented. Accordingly, it is possible to efficiently perform the training of the machine learning model in which the food and drink data is used, by controlling the training of the machine learning model in accordance with the input result in response to such detailed selection reasons.

In addition, the controlling of the training may include: determining a parameter for the training according to the result of the input in response to the selection reasons; and controlling the training using the parameter.

In this manner, an optimal parameter for the training of the machine learning model is determined according to an input result in response to the selection reasons, and thus it is possible to efficiently perform the training of the machine learning model using the optimal parameter.

In addition, the parameter may be a weighting parameter of the food and drink data.

In this manner, a weighting parameter of the food and drink data is determined according to an input result in response to the selection reasons, and thus it is possible to efficiently perform the training of the machine learning model using the weighting parameter.

In addition, the parameter may be a reward in reinforcement learning.

In this manner, a reward in the reinforcement learning is determined according to an input result in response to the selection reasons, and thus it is possible to efficiently perform the training of the machine learning model using the reward in the reinforcement learning.

In addition, in the determining of the parameter, the parameter for the training may be determined additionally according to a result of an input in response to the options.

In this manner, it is possible to improve the effect of the training, by controlling the training using additionally an input of the option related to the input of the selection reason.

In addition, (i) the result of the input in response to the selection reasons may include at least one of a direction, a strength, or a speed of the input in response to the selection reasons; or (ii) a result of an input in response to the options may include at least one of a direction, a strength, or a speed of the input in response to the options.

As described above, it is possible to efficiently perform the training of the machine learning model, according to the direction, the strength, or the speed of an input in response to the selection reasons or the options.

In addition, in the determining of the parameter, when the input in response to the selection reasons is not immediately made, the parameter determined may be a parameter with which an effect of the training is reduced.

When the input in response to the selection reasons is not immediately made, it is considered that the user has made the input in response to the selection reasons after wavering, and thus there is a possibility that the selection reason that has been input at this time is not applicable to the user. In view of the above, when the input in response to the selection reasons is not immediately made, it is possible to efficiently perform the training of the machine learning model, by determining a parameter for a training with which an effect of the training is reduced.

In addition, in the determining of the parameter, when the input in response to the selection reasons is immediately made, the parameter determined may be a parameter with which an effect of the training is increased.

When an input in response to the selection reasons is immediately made, it is considered that the user has made the input without wavering about the selection reason, and thus there is a possibility that the selection reason that has been input at this time is applicable to the user. In view of the above, when the input in response to the selection reasons is immediately made, it is possible to efficiently perform the training of the machine learning model, by determining a parameter for a training with which an effect of the training is increased.

In addition, the presenting of the selection reasons may be controlled according to at least one of the speed or the strength of the input in response to the options.

In this manner, for example, when an input in response to the options is made with a high speed or a high strength, it is considered that the user has input the option judging by the appearance of an image of the presented food and drink data, and thus it is possible to present selection reasons that are related to appearances. In addition, for example, when an input in response to the options is made with a low speed or a low strength, it is considered that the user has input the option after wavering, and thus there is a high possibility that the selection reason in this case are not applicable to the user. Accordingly, it is possible to present another specific selection reason.

In addition, in the controlling of the training, whether to perform the training may be determined according to the result of the input in response to the selection reasons.

In this manner, it is possible to efficiently perform the training of a machine learning model, by performing the training when an input result in response to the selection reasons is data with high learning efficiency and not performing the training when an input result in response to the selection reasons is data with low learning efficiency. In addition, since data with low learning efficiency is not collected, it is possible to reduce the storage capacity for storing data for the training of a machine learning model.

In addition, the machine learning model my output a prediction value regarding selection from among the options for the food and drink data, the prediction value being obtained by inputting the food and drink data into the machine learning model, the prediction value may be obtained from the machine learning model, and the selection reasons for the food and drink data of which the prediction value is greater than or equal to a threshold may be not presented.

In this manner, for the food and drink data of which the prediction value regarding the selection from among the option is greater than or equal to a threshold, the training regarding which option is to be selected has been advanced, and it is thus possible to avoid presenting selection reasons for such food and drink data. In other words, it is possible to prevent the user from having to be bothered to input a selection reason.

In addition, when the result of the input in response to the options is positive, other food and drink data associated with the food and drink data may be presented via the presentation device.

In this manner, for example, in the case where a menu of a meal is proposed by presenting options for food and drink data, when an input result in response to the options for the presented food and drink data is positive, it is possible to present, as other food and drink data that is associated with the presented food and drink data, food and drink data which can constitute a better meal in combination with the presented food and drink data (for example, a side dish that matches a main dish).

In addition, when the result of the input in response to the options is negative, next food and drink data may be determined based on the result of the input in response to the selection reasons, and presented via the presentation device.

In this manner, when an input result in response to the options for the food and drink data that has been presented is negative, it is possible to present next food and drink data that is different from the presented food and drink data.

In addition, attributes of the food and drink data may be presented via the presentation device, and in the presenting of the selection reasons, the selection reasons corresponding to the attributes may be generated and presented via the presentation device.

The selection reasons for the options for food and drink data include various reasons for each of the attributes such as an ingredient, a recipe, a seasoning, etc. of the food and drink data. In view of this, it is possible to efficiently perform the training of a machine learning model, by generating and presenting selection reasons that correspond to the attributes, and controlling the training of the machine learning model according to a result of an input in response to the selection reasons for each of the attributes.

In addition, the machine learning model may output a prediction value regarding whether to adopt the selection reasons for each of the attributes of the food and drink data, the prediction value being obtained by inputting the food and drink data into the machine learning model, the prediction value may be obtained from the machine learning model, and the selection reasons for the attribute of which the prediction value is greater than or equal to the threshold may be not presented.

In this manner, an attribute of which a prediction value regarding whether to adopt the selection reasons is greater than or equal to a threshold, the training regarding which of the selection reasons is to be selected has been advanced, and it is thus possible to avoid presenting selection reasons for such an attribute. In other words, it is possible to prevent the user from having to be bothered to input a selection reason.

In addition, when the result of the input in response to the options is negative, the food and drink data of which the attributes are different may be determined based on the result of the input in response to the selection reasons, and presented via the presentation device.

In this manner, when an input result in response to the options for the food and drink data that has been presented is negative, it is possible to present food and drink data that is different in attributes (for example, different in the ingredient, the recipe, the seasoning, or the like) from the presented food and drink data.

In addition, the selection reasons may be generated based on a feature of the food and drink data.

For example, food and drink data includes an image of the food and drink, a dish name of the food and drink, or the like, and it is possible to generate selection reasons based on a feature of these information items.

In addition, an input in response to the options and the input in response to the selection reasons may be made by flick input.

According to this, it is possible to easily input an option and a selection reason by flick input.

In addition, a sound obtained during the flick input may be obtained as the result of the input in response to the selection reasons.

According to this, it is possible to input a selection reason by a sound during the flick input.

An information processing system according to one aspect of the present disclosure includes an obtainer that obtains food and drink data; an option generator that generates options for the food and drink data; a selection reason generator that generates selection reasons corresponding to an option selected from among the options; a presentation controller that presents the food and drink data, the options, and the selection reasons, via the presentation device; and a controller that controls training of a machine learning model according to a result of an input in response to the selection reasons, the training using the food and drink data.

According to this configuration, it is possible to provide an information processing system capable of efficiently performing training of a machine learning model, in which food and drink data is used.

The following describes in detail an embodiment with reference to the drawings.

Each of the embodiments described below shows a general or specific example. The numerical values, shapes, materials, structural components, the arrangement and connection of the structural components, steps, the processing order of the steps, etc. shown in the following embodiments are mere examples, and therefore do not limit the scope of the claims of present disclosure.

Embodiment

The following describes an embodiment with reference to FIG. 1 through FIG. 5.

FIG. 1 is a block diagram illustrating one example of server 100 and presentation device 200 according to the embodiment.

Server 100 is a device that communicates with presentation device 200 and presents contents to presentation device 200, and is one example of an information processing system. For example, server 100 has a function of proposing a meal to a user of presentation device 200. In addition, server 100 has a function of obtaining a response to a proposal to the user from presentation device 200, and learning a preference of the user in regard to food and drink.

Server 100 includes: content proposer 110; trainer 120; storage 130; and communication section 140. Server 100 is a computer that includes a processor, a memory, a communication interface, etc. The memory is a read only memory (ROM), a random access memory (RAM), etc., and is capable of storing a program that is executed by a processor. It should be noted that storage 130 is one example of the memory, but may be a memory different from the memory that stores a program. Content proposer 110 and trainer 120 are implemented by a processor or the like that executes a program stored in the memory. Communication section 140 is implemented by a communication interface that includes, for example, a connector to which a communication circuit, a communication line, etc. are connected, or an antenna. It should be noted that the structural components included in server 100 may be dispersedly arranged in a plurality of servers.

Storage 130 stores food and drink data and a machine learning model for which the food and drink data is used.

Content proposer 110 is one example of an obtainer that obtains food and drink data from storage 130, an option generator that generates options that correspond to the food and drink data, a selection reason generator that generates selection reasons corresponding to an option that has been selected from among the options, and a presentation controller that presents the food and drink data, the options, and the selection reasons via presentation device 200. The operations performed by content proposer 110 will be described later in detail.

Communication section 140 is a communication interface that performs communication with presentation device 200. Communication section 140 transmits the food and drink data obtained by content proposer 110 and the options and the selection reasons which have been generated by content proposer 110, to presentation device 200. More specifically, communication section 140 transmits, to presentation device 200, user interface (UI) data for presenting the food and drink data, the options, and the selection reasons on presentation device 200. In addition, communication section 140 receives, from presentation device 200, input results that are a result of an input in response to the options and a result of an input in response to the selection reasons, which have been provided using presentation device 200.

Trainer 120 is one example of a controller that controls training of the machine learning model, in which the food and drink data is used, according to an input result in response to the selection reasons. Trainer 120 controls the training of a machine learning model stored in storage 130. In this manner, user's preferences in regard to the food and drink is learned. The operations performed by trainer 120 will be described later in detail.

Presentation device 200 is a device that communicates with server 100 and presents, to a user, content provided by server 100. Examples of presentation device 200 include a smartphone, a tablet terminal, etc.

Presentation device 200 includes: presentation controller 210; presentation section 220; inputting section 230; and communication section 240. Presentation device 200 is a computer that includes a processor, a memory, a user interface, a communication interface, etc. The memory is a ROM, a RAM, etc., and is capable of storing a program that is executed by a processor. Presentation controller 210 is implemented by a processor or the like that executes a program stored in the memory. Communication section 240 is implemented by a communication interface that includes a communication circuit, an antenna, etc. For example, presentation section 220 and inputting section 230 are shown as separate components, but may be a single component having a presentation function and an input function.

Communication section 240 is a communication interface that communicates with server 100. Communication section 240 receives food and drink data, options, and selection reasons from server 100. More specifically, communication section 240 receives, from server 100, UI data for presenting the food and drink data, the options, and the selection reasons on presentation device 200. In addition, communication section 240 transmits, to server 100, input results including a result of an input in response to the options and a result of an input in response to the selection reasons, which have been provided using presentation device 200.

Presentation controller 210 presents, on presentation section 220, the food and drink data, the options, and the selection reasons to presentation section 220, based on the UI data received by communication section 240. In addition, presentation controller 210 controls presentation on presentation section 220 according to an input to inputting section 230. The operations performed by presentation controller 210 will be described later in detail.

Presentation section 220 is, for example, a touch panel display that presents food and drink data, options, and selection reasons. The details of presentation on presentation section 220 change according to the input to inputting section 230.

Inputting section 230 is an input device that receives a user operation, and is, for example, a touch panel display. The user performs selection from among the options presented on presentation section 220 and determines whether to adopt the selection reasons, by performing a flick input (i.e., a flick operation), for example. The selected option is an input result in response to the options, and the adopted selection reason is an input result in response to the selection reasons.

Next, the operation of server 100 will be described with reference to FIG. 2A, FIG. 2B, and FIG. 5, and the operations of presentation device 200 will be described with reference to FIG. 3. It should be noted that the information processing method according to the embodiment may be, for example, a method executed by a processor included in server 100, and the steps illustrated in FIG. 2A, FIG. 2B, and FIG. 5 may be processes performed via the information processing method according to the embodiment.

Figure 2A:
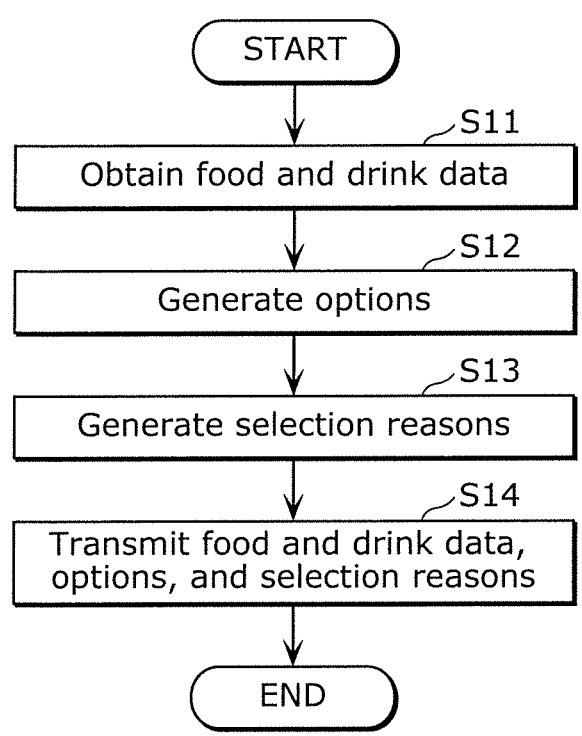

FIG. 2A is a flowchart illustrating one example of the operation of server 100 according to the embodiment when server 100 transmits food and drink data and the like.

Content proposer 110 (obtainer) obtains food and drink data from storage 130 (Step S11). Various kinds of food and drink data are stored in storage 130. For example, the food and drink data is obtained at random or according to a predetermined rule. For example, the food and drink data includes: data such as a dish name, an image, ingredient, a recipe, seasonings, a genre, a difficulty level of cooking, and cooking time of the food and drink; and metadata.

Next, content proposer 110 (option generator) generates options for the food and drink data that has been obtained (Step S12). For example, the options are options regarding whether or not to adopt the food and drink data for today's meal, and more specifically, the options are presented, for example, as "Yes" and "No" on presentation device 200. For example, when the option "Yes" is selected, the food and drink data is adopted for today's meal, and when the option "No" is selected, the food and drink data is not adopted for today's meal.

Next, content proposer 110 (selection reason generator) generates selection reasons corresponding to an option that has been selected (Step S13). For example, the selection reasons are candidates for a reason to adopt the obtained food and drink data for today's meal, candidates for a reason not to adopt the obtained food and drink data for today's meal, etc. More specifically, the selection reasons are presented as, for example, "I like it", "I dislike it", and "I ate it yesterday" on presentation device 200.

Then, communication section 140 transmits the food and drink data, the options, and the selection reasons to presentation device 200 (Step S14). More specifically, communication section 140 transmits, to presentation device 200, UI data that includes the food and drink data, the options, and the selection reasons. As a result, the options and the selection reasons are presented on presentation device 200, and thus content proposer 110 (presentation controller) presents the food and drink data, the options, and selection reasons via presentation device 200.

It should be noted that, when the training is advanced to some extent, the machine learning model for which training is controlled by trainer 120 may output a prediction value regarding selection from among the options for food and drink data, which has been obtained by inputting the food and drink data into the machine learning model. In other words, the machine learning model may output a prediction value regarding whether or not a user adopts, for a meal, the food and drink data that has been input. For example, generation of selection reasons may be controlled using such a machine learning model. This will be described with reference to FIG. 2B.

Figure 2B:
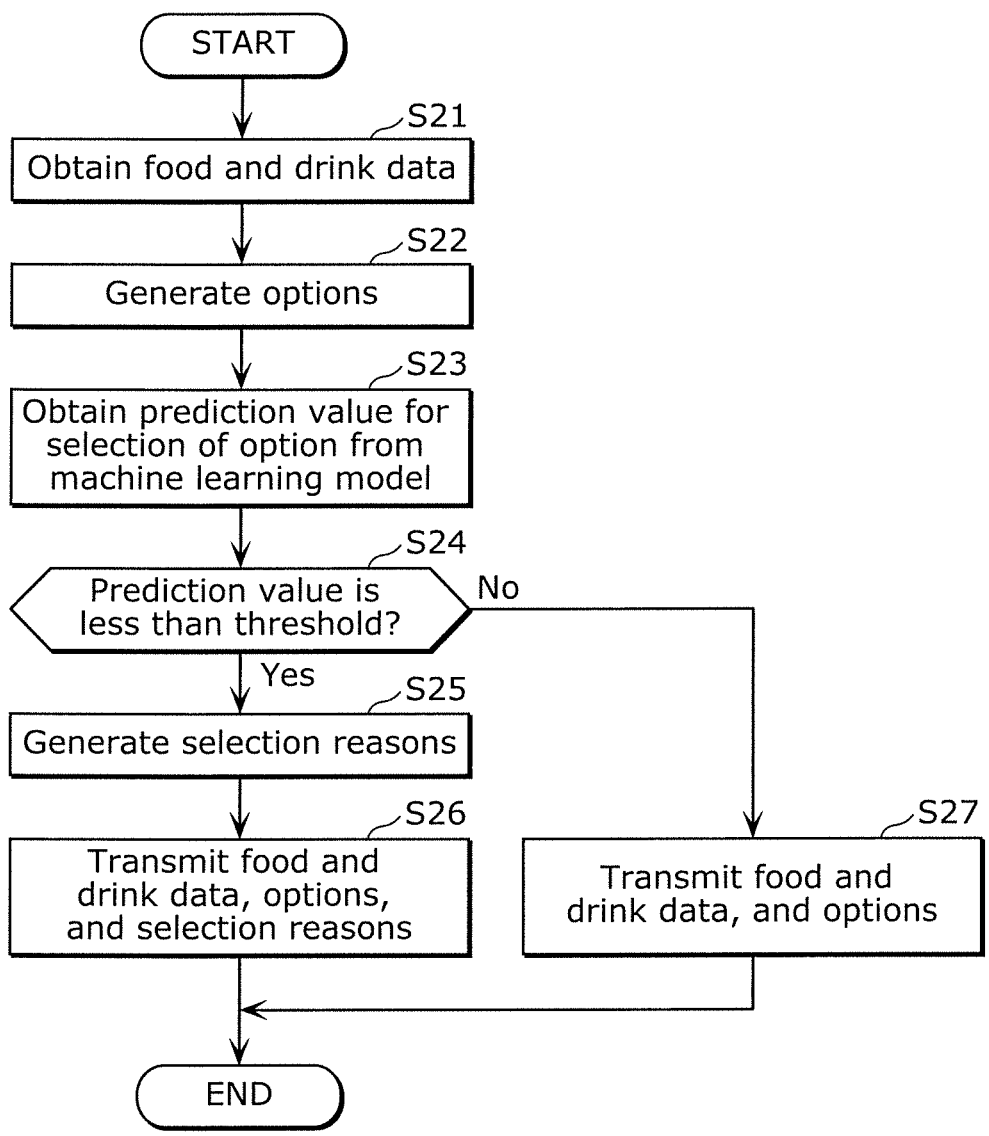

FIG. 2B is a flowchart illustrating another example of the operation of server 100 according to the embodiment when transmitting food and drink data and the like.

Content proposer 110 obtains the food and drink data from the storage 130 (Step S21), and generates options for the food and drink data that has been obtained (Step S22).

Next, content proposer 110 obtains a prediction value regarding selection from among the options for the food and drink data output from the machine learning model (Step S23). For example, as a result of the training, when it is predicted that the user is highly likely to adopt, for the meal, the food and drink data that has been input to the machine learning model, that is, when it is predicted that the user is highly likely to select the option "Yes" on presentation device 200, the prediction value for the selection of the option "Yes" increases. In addition, when it is predicted that the user is highly likely not to adopt, for the meal, the food and drink data that has been input to the machine learning model, that is, when it is predicted that the user is highly likely to select the option "No" on presentation device 200, the prediction value for the selection of the option "No" increases. On the other hand, when it is not clear whether the user selects the option "Yes" or the option "No", the prediction value decreases.

Next, content proposer 110 determines whether or not the obtained prediction value is less than a threshold (Step S24).

When the obtained prediction value is less than the threshold (Yes in Step S24), content proposer 110 generates selection reasons (Step S25). When the prediction value is less than the threshold, it is not clear whether the user selects the option "Yes" or the option "No", and thus it is necessary to present selection reasons on presentation device 200 to cause the user to select and input a selection reason, and further perform training, using an input result in response to the selection reasons, on the machine learning model regarding the food and drink data with the prediction value being less than the threshold value.

Then, communication section 140 transmits the food and drink data, the options, and the selection reasons to presentation device 200 (Step S26).

When the obtained prediction value is greater than or equal to the threshold, content proposer 110 does not generate selection reasons, and communication section 140 transmits the food and drink data and the options to presentation device 200 (Step S27). In other words, content proposer 110 does not present the selection reasons for the food and drink data with the prediction value being greater than or equal to the threshold. This is because it is clear whether the user selects the option "Yes" or the option "No" when the prediction value is greater than or equal to the threshold, and thus it is not necessary to present selection reasons on presentation device 200 to cause the user to select and input a selection reason. Accordingly, there is no need to further perform training, using an input result, on the machine learning model regarding the food and drink data with the prediction value being greater than or equal to the threshold value. As described above, for the food and drink data of which the prediction value regarding selection from among the options is greater than or equal to a threshold, the training regarding which option is to be selected has been advanced, and it is thus possible to avoid presenting selection reasons for such food and drink data. In other words, it is possible to prevent the user from having to be bothered to input a selection reason.

Figure 3:
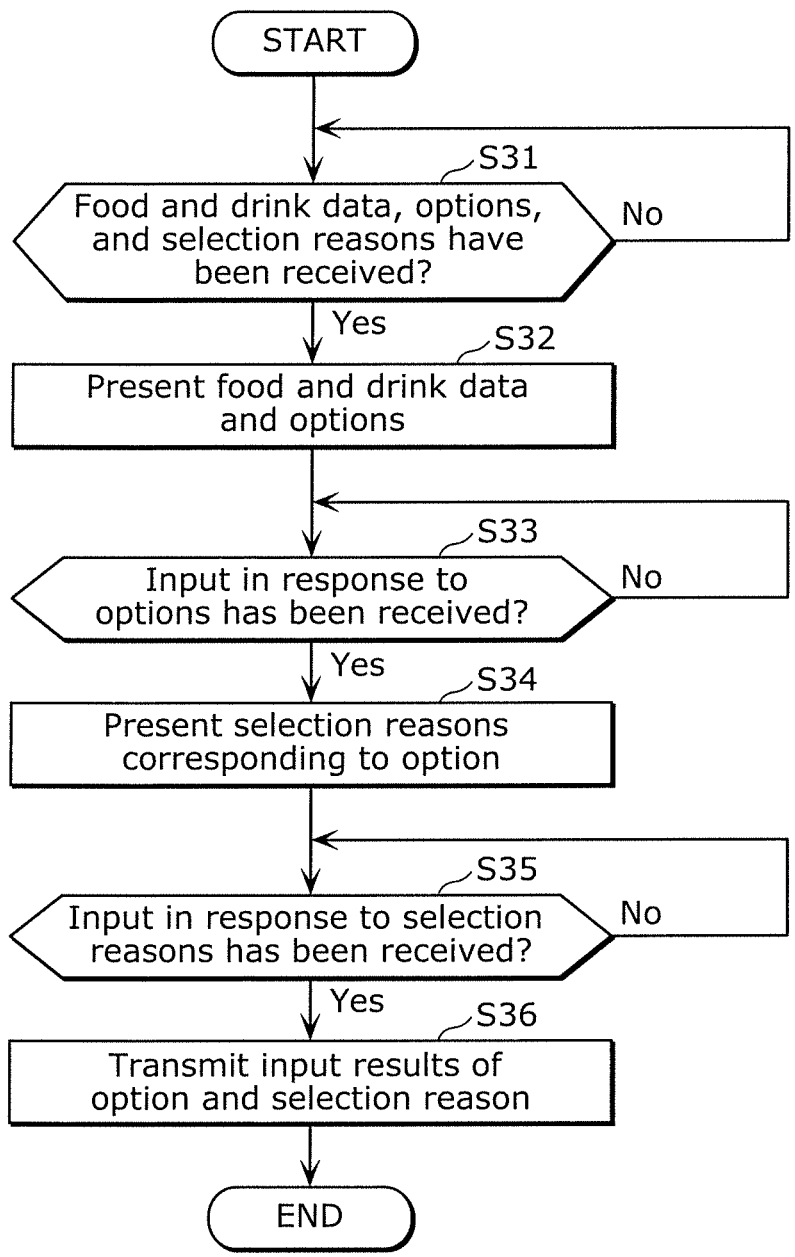
FIG. 3 is a flowchart illustrating one example of the operation performed by the presentation device according to the embodiment.

FIG. 3 is a flowchart illustrating one example of the operation performed by presentation device 200 according to the embodiment.

Presentation controller 210 determines whether communication section 240 has received the food and drink data, the options, and the selection reasons from server 100 (Step S31). More specifically, presentation controller 210 determines whether or not communication section 240 has received UI data that includes the food and drink data, the options, and the selection reasons from server 100.

When presentation controller 210 determines that communication section 240 has not received the food and drink data, the options, and the selection reasons from server 100

(No in Step S31), the process in Step S31 is repeatedly performed until communication section 240 receives the food and drink data, the options, and the selection reasons.

When presentation controller 210 determines that communication section 240 has received the food and drink data, the options, and the selection reasons from server 100 (Yes in Step S31), presentation controller 210 presents the food and drink data and the options on presentation section 220 (Step S32). More specifically, presentation controller 210 generates an image of the food and drink data and an image of the options using the UI data that includes the food and drink data, the options, and the selection reasons, and presents these images on presentation section 220.

Next, presentation controller 210 determines whether an input in response to the options presented on presentation section 220 has been received (Step S33). More specifically, presentation controller 210 determines whether or not a user operation in response to the options presented on presentation section 220 has been received via inputting section 230.

When an input in response to the options presented on presentation section 220 has not been received (No in Step S33), presentation controller 210 repeats the process in Step S33 until an input in response to the options presented on presentation section 220 is received.

When an input in response to the options presented on presentation section 220 has been received (Yes in Step S33), presentation controller 210 presents selection reasons corresponding to the option that has been selected (Step S34). More specifically, presentation controller 210 generates an image of the selection reason according to the option that has been selected, using the UI data that includes the food and drink data, the options, and the selection reasons, and presents the image on presentation section 220.

Here, the image of the food and drink data and the image of the options presented on presentation section 220, and the image of the selection reasons presented when an input in response to the presented options has been received will be described with reference to FIG. 4.

Figure 4:
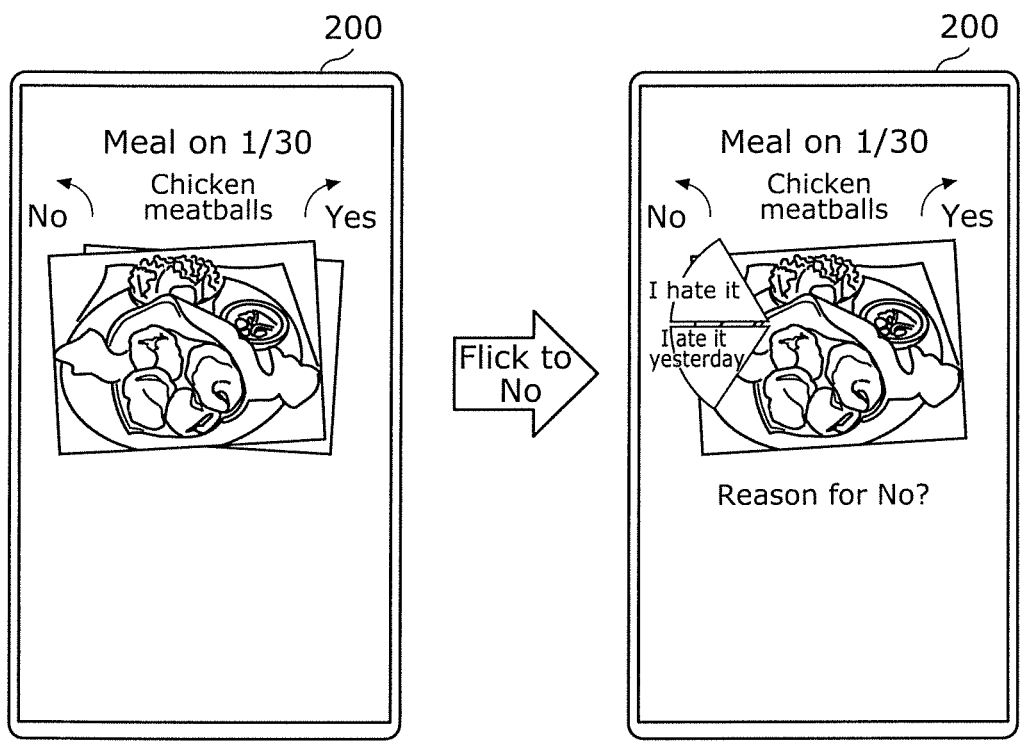
FIG. 4 is a diagram illustrating one example of the images presented on the presentation device according to the embodiment.

FIG. 4 is a diagram illustrating one example of the images presented on presentation device 200 according to the embodiment. On the left side of FIG. 4, an image of the food and drink data and an image of the options presented on presentation device 200 are illustrated. On the right side of FIG. 4, an image of the food and drink data, an image of the options, and an image of selection reasons presented on presentation device 200 are illustrated.

As illustrated on the left side of FIG. 4, in the processing in Step S32, an image of chicken meatballs, for example, is presented as an image of the food and drink data on presentation device 200, and an image including an option image "Yes" and an option image "No", for example, is presented as an image of the options on presentation device 200. In addition, an image of an arrow prompting a flick input toward the side on which "Yes" is presented on the screen is presented in proximity to the option image "Yes", and an image of an arrow prompting a flick input toward the side on which "No" is presented on the screen is presented in proximity to the option image "No". A user who has seen these images performs a flick input toward the side on which the option image "Yes" is presented when adopting the chicken meatballs for the meal. When the user does not adopt the chicken meatballs for the meal, the user performs a flick input toward the side on which the option image "No" is presented. In the above-described manner, the user can perform an input in response to the options.

For example, it is assumed that the user has performed a flick input toward the side on which the option image "No" is presented. In this case, as illustrated on the right side of FIG. 4, an image of selection reasons for selecting "No", that is, an image of the reasons for not adopting the chicken meatballs for the meal, is presented as an image of the selection reasons corresponding to the option, on the side on which "No" is presented on the screen. Here, an image including a selection reason image "I hate it" and a selection reason image "I ate it yesterday" is presented as an image of the selection reasons corresponding to the option "No". When the reason for not adopting the chicken meatballs for the meal is that the user hates chicken meatballs, the user performs a flick input toward the selection reason image "I hate it". When the reason for not adopting the chicken meatballs for the meal is that the user ate chicken meatballs yesterday, the user performs a flick input toward the selection reason image "I ate it yesterday". In this manner, the user can perform an input in response to the detailed selection reasons.

Returning back to the description of FIG. 3, presentation controller 210 determines whether or not an input in response to the selection reasons presented on presentation section 220 has been received (Step S35). More specifically, presentation controller 210 determines whether a user operation for the selection reasons presented on presentation section 220 has been received via inputting section 230.

In the case where an input in response to the selection reasons presented on presentation section 220 has not been received (No in Step S35), presentation controller 210 repeats the process in Step S35 until an input in response to the selection reasons presented on presentation section 220 is received.

In the case where an input in response to the selection reasons presented on presentation section 220 has been received (Yes in Step S35), presentation controller 210 transmits input results in response to the options and the selection reasons via communication section 240 to server 100 (Step S36). For example, when the user does not adopt chicken meatballs for the meal and the reason therefor is that the user hates chicken meatballs, the input result in response to the options indicates that the chicken meatballs are not adopted, and the input result in response to the selection reasons indicates that the reason for not adopting the chicken meatballs is that the user hates chicken meatballs.

It should be noted that, when the selection reason is not received in Step S31, that is, when food and drink data and options are transmitted and selection reasons are not transmitted from server 100 as in Step S27 in FIG. 2B, the processes of Step S34 and Step S35 need not be performed, and an input result in response to the selection reasons need not be transmitted in Step S36.

Figure 5:
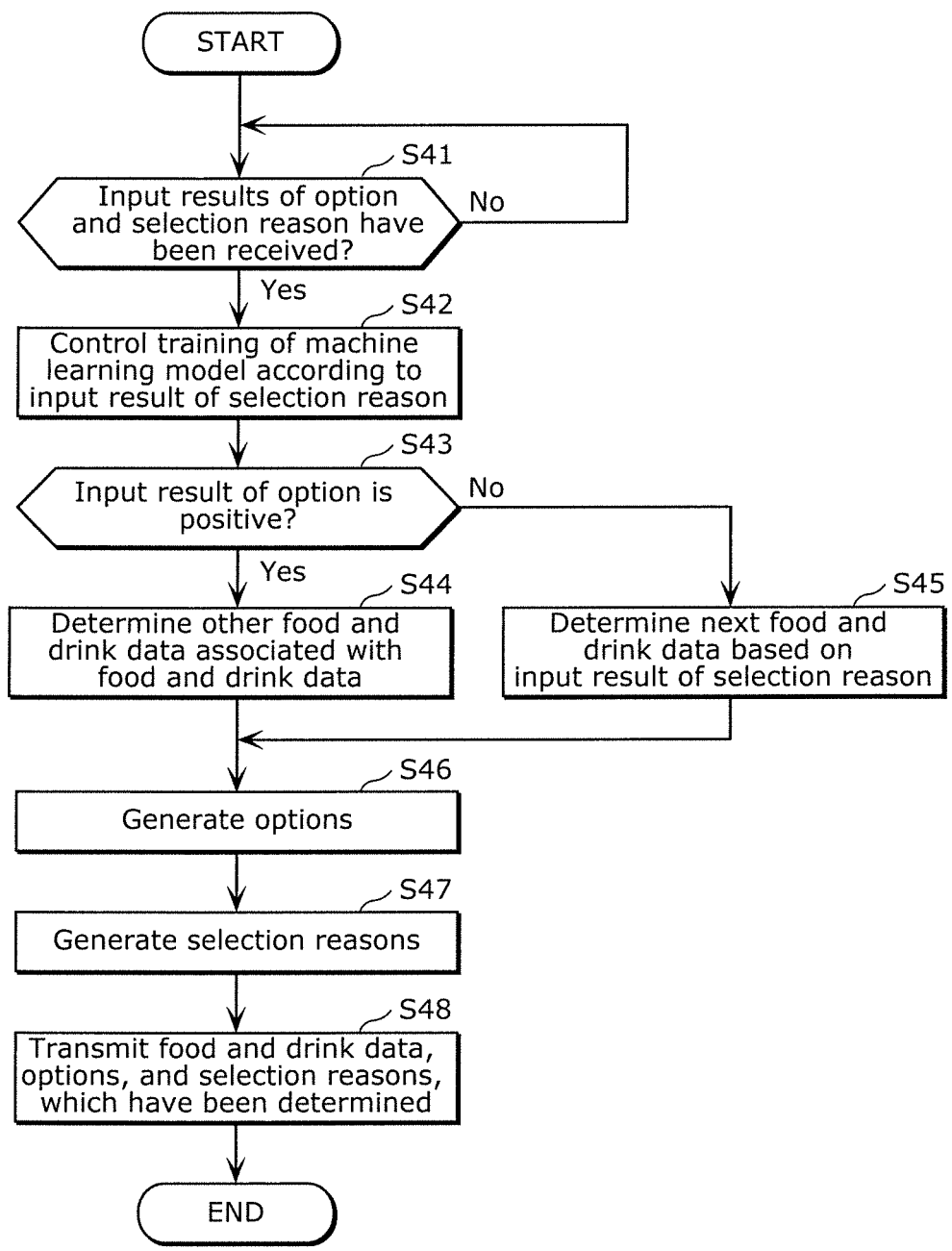
FIG. 5 is a flowchart illustrating one example of the operation performed by the server according to the embodiment when the server receives an input result.

FIG. 5 is a flowchart illustrating one example of the operation of server 100 according to the embodiment when server 100 receives input results.

Trainer 120 determines whether communication section 140 has received input results in response to options and selection reasons from presentation device 200 (Step S41).

When trainer 120 determines that communication section 140 has not received input results in response to the options and the selection reasons from presentation device 200 (No in Step S41), communication section 140 repeatedly performs the process in Step S41 until communication section 140 receives the input results in response to the options and the selection reasons.

When trainer 120 determines that communication section 140 has received input results in response to the options and the selection reasons from presentation device 200 (Yes in Step S41), trainer 120 controls the training of a machine learning model, in which the food and drink data is used, according to the input result in response to the selection reasons (Step S42).

For example, trainer 120 may determine a parameter for the training according to the input result in response to the selection reasons, and train the machine learning model with the parameter that has been determined. The parameter for the training is, for example, a weighting parameter of food and drink data. For example, trainer 120 determines a weighting of an input vector corresponding to the selection reason, according to the input result in response to the selection reasons. In addition, the parameter for the training may be a reward in reinforcement learning. For example, when the selection reason that has been selected is "I hate it", trainer 120 trains the model in such a way that the food and drink data "chicken meatballs" is less likely to be proposed as a meal candidate, with a parameter with which an effect of the training is increased. In addition, for example, when the selection reason that has been selected is "I ate it yesterday", trainer 120 trains the model in such a way that the food and drink data "chicken meatballs" is less likely to be proposed as a meal candidate, a parameter with which an effect of the training is reduced.

In addition, for example, trainer 120 may determine a parameter for the training according to the input result in response to the options. The input of the option is related to the input of the selection reason, and it is possible to improve the effect of the training, by controlling the training additionally using such an input of the option related to the selection reason.

It should be noted that the input result in response to the selection reasons or the input result in response to the options may include the direction, strength, or speed of the input regarding the selection reason or the input regarding the option. For example, when the input regarding the option or the selection reason is made a flick input, the input result in response to the selection reasons or the input result in response to the options may include the direction, the strength, or the speed of the flick input when the flick input is performed regarding the selection reason or the option.

For example, when the input in response to the selection reasons is not immediately made, trainer 120 determines a parameter for the training with which the effect of the training is reduced. For example, when the input in response to the selection reasons is not immediately made, trainer 120 sets a weighting parameter of the food and drink data to a low value. This is because, when the input in response to the selection reasons is not immediately made, it is conceived that the user has input the selection reason after wavering, and there is a possibility that the selection reason that has been input at this time is not applicable to the user.

For example, when the input in response to the selection reasons is immediately made, trainer 120 determines a parameter for the training with which the effect of the training is increased. For example, when the input in response to the selection reasons is immediately made, trainer 120 sets a weighting parameter of the food and drink data to a high value. This is because, when the input in response to the selection reasons is immediately made, it is conceived that the user has input the selection reason without wavering, and there is a possibility that the selection reason that has been input at this time is applicable to the user.

In addition, for example, trainer 120 may determine whether or not to perform the training according to the input result in response to the selection reasons. More specifically, trainer 120 may skip the training of the machine learning model depending on the input result in response to the selection reasons. For example, it is possible to efficiently perform the training of the machine learning model, by performing the training when the input result in response to the selection reasons is data that is efficient in learning, and not performing the training when the input result in response to the selection reasons is data that is inefficient in learning. In addition, since data that is inefficient in learning is not collected, it is possible to reduce the storage capacity for storing data for training the machine learning model. For example, when the selection reason that has been selected is "I hate it", trainer 120 trains the model so that the food and drink data "Chicken meatballs" is less likely to be proposed as a meal candidate. When the selection reason that has been selected is "I ate it yesterday", trainer 120 does not perform training regarding the food and drink data "Chicken meatballs".

Next, trainer 120 determines whether or not the input result in response to the options is positive (Step S43). For example, when the user performs a flick input toward the side on which the option image "Yes" is presented, the input result in response to the options is positive, and when the user performs a flick input toward the side on which the option image "No" is presented, the input result in response to the options is negative.

When the input result in response to the options is positive (Yes in Step S43), content proposer 110 determines other food and drink data that is associated with the food and drink data (Step S44). The case where the input result in response to the options is positive is, for example, the case where the presented food and drink data is adopted for the meal. The other food and drink data associated with the food and drink data adopted for the meal is food and drink data that goes well together with the food and drink data adopted for the meal. Specifically, when the adopted food and drink data indicates Japanese main dish, the other food and drink data is data indicating Japanese side dish, Japanese soup, or the like that matches the Japanese main dish.

On the other hand, when the input result in response to the options is negative (No in Step S43), content proposer 110 determines the next food and drink data, based on the input result in response to the selection reasons (Step S45). The case where the input result in response to the options is negative is, for example, the case where the presented food and drink data is not adopted for the meal. The next food and drink data is food and drink data that does not correspond to the selection reason for not adopting the presented food and drink data. For example, when the presented food and drink data indicates chicken meatballs that is the main dish, and the selection reason for not adopting it indicates that the user ate it yesterday, the next food and drink data is food and drink data that is different from the food and drink data included in the meal of yesterday, and can be a main dish.

Then, content proposer 110 generates options additionally for the food and drink data that has been determined (Step S46), and generates selection reasons that correspond to the options (Step S47), and communication section 140 transmits the food and drink data that has been determined, the options, and the selection reasons to presentation device 200 (Step S48). As a result, content proposer 110 additionally presents the food and drink data which has been determined via presentation device 200, and the processes illustrated in FIG. 2A, FIG. 2B, FIG. 3, and FIG. 5 are performed.

It should be noted that, when some items of the food and drink data are adopted and all the meal components are determined, the processing may be ended without performing the process of Step S43 and the processes subsequent to Step S43.

It should be noted that, when an input result in response to the selection reasons is not received in Step S41, that is, when food and drink data and options are transmitted and selection reasons are not transmitted from server 100 as in Step S27 in FIG. 2B, and an input result of a selection reason is not transmitted in Step S36 in FIG. 3, the processes of Step S42 need not be performed.

It should be noted that, it is not necessary to repeat, for each item of food and drink data, presenting once the food and drink data, the options, and the selection reasons, and controlling the training of the machine learning model according to the input results. More specifically, a plurality of items of food and drink data and the respective options and selection reasons of the plurality of items of food and drink data may be collectively transmitted to presentation device 200. In this case, presentation device 200 may repeat the processes from Step S32 to Step S35 in FIG. 3 for each of the plurality of items of food and drink data which have been received, and input results in response to the respective options and selection reasons of the plurality of items of food and drink data may be transmitted to server 100. Then, the training of the machine learning model may be controlled according to the input results in response to the respective options and the selection reasons of the plurality of items of food and drink data.

As described above, for example, there are instances where the user's impression of the food and drink data is ambiguous because it varies depending on the current weather, the user's physical condition, mood, schedule, and the like. Accordingly, there is a possibility that such ambiguous data may be data that is inefficient in learning for the machine learning model for which the food and drink data is used. In view of the above-described circumstances, selection reasons (specifically, a plurality of selection reason candidates) are generated in accordance with the options for the food and drink data, and the generated selection reasons are presented on the presentation device to cause the user to select and input a selection reason from among the presented selection reasons. The input result in response to the selection reasons is adopted by the user not based on the impression that the user may come up with from moment to moment but from the selection reasons generated in detail and presented. Accordingly, it is possible to efficiently perform the training of the machine learning model, in which the food and drink data is used, by controlling the training of the machine learning model in accordance with the input result in response to such detailed selection reasons.

(Variation)

The following describes a variation of the embodiment with reference to FIG. 6A to FIG. 10.

The configurations of server 100 and presentation device 200 according to the variation of the embodiment are the same as configurations of server 100 and presentation device 200 according to the embodiment, but the functions are different from those in the embodiment.

Figure 6A:
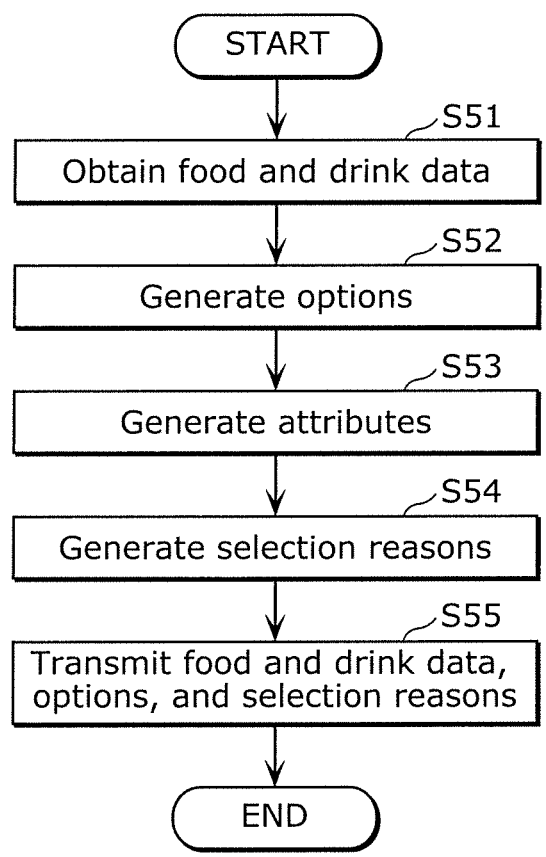

FIG. 6A is a flowchart illustrating one example of the operation of server 100 according to the variation of the embodiment when server 100 transmits food and drink data and the like.

Content proposer 110 obtains the food and drink data from storage 130 (Step S51), and generates options for the food and drink data that has been obtained (Step S52).

Next, content proposer 110 generates attributes of the food and drink data (Step S53). The attributes of the food and drink data are, for example, an ingredient, a recipe, a seasoning, and the like of the food and drink data, and specifically, are presented on presentation device 200 as "Ingredient", "Recipe", and "Taste".

Next, content proposer 110 generates selection reasons corresponding to the attributes (Step S54). For example, the selection reasons corresponding to the attributes include candidates of the reason when the attribute is focused among the reasons for adopting the obtained food and drink data for today's meal, and candidate of the reason when the attribute is focused among the reasons for not adopting the obtained food and drink data for today's meal. More specifically, the selection reasons corresponding to the attribute are presented as, for example, "I like it", "I dislike it", "I ate it yesterday", etc. on presentation device 200.

Then, communication section 140 transmits the food and drink data, the options, the attributes, and the selection reasons to presentation device 200 (Step S55). More specifically, communication section 140 transmits the UI data that includes the food and drink data, the options, the attributes, and the selection reasons to presentation device 200. As a result, the options, the attributes, and the selection reasons are presented on presentation device 200, and thus content proposer 110 presents the options, the attributes, and the selection reasons via presentation device 200.

It should be noted that the machine learning model for which training is controlled by trainer 120 may output a prediction value regarding whether to adopt the selection reason for each of the attributes of the food and drink data which are obtained by inputting the food and drink data into the machine learning model, when the training is advanced to some extent. In other words, the machine learning model may output, for each of the attributes, a prediction value regarding whether the user adopts each of the selection reasons corresponding to the attribute of the food and drink data that has been input. For example, generation of the selection reasons corresponding to an attribute may be controlled by using such a machine learning model. This will be described with reference to FIG. 6B.

Figure 6B:
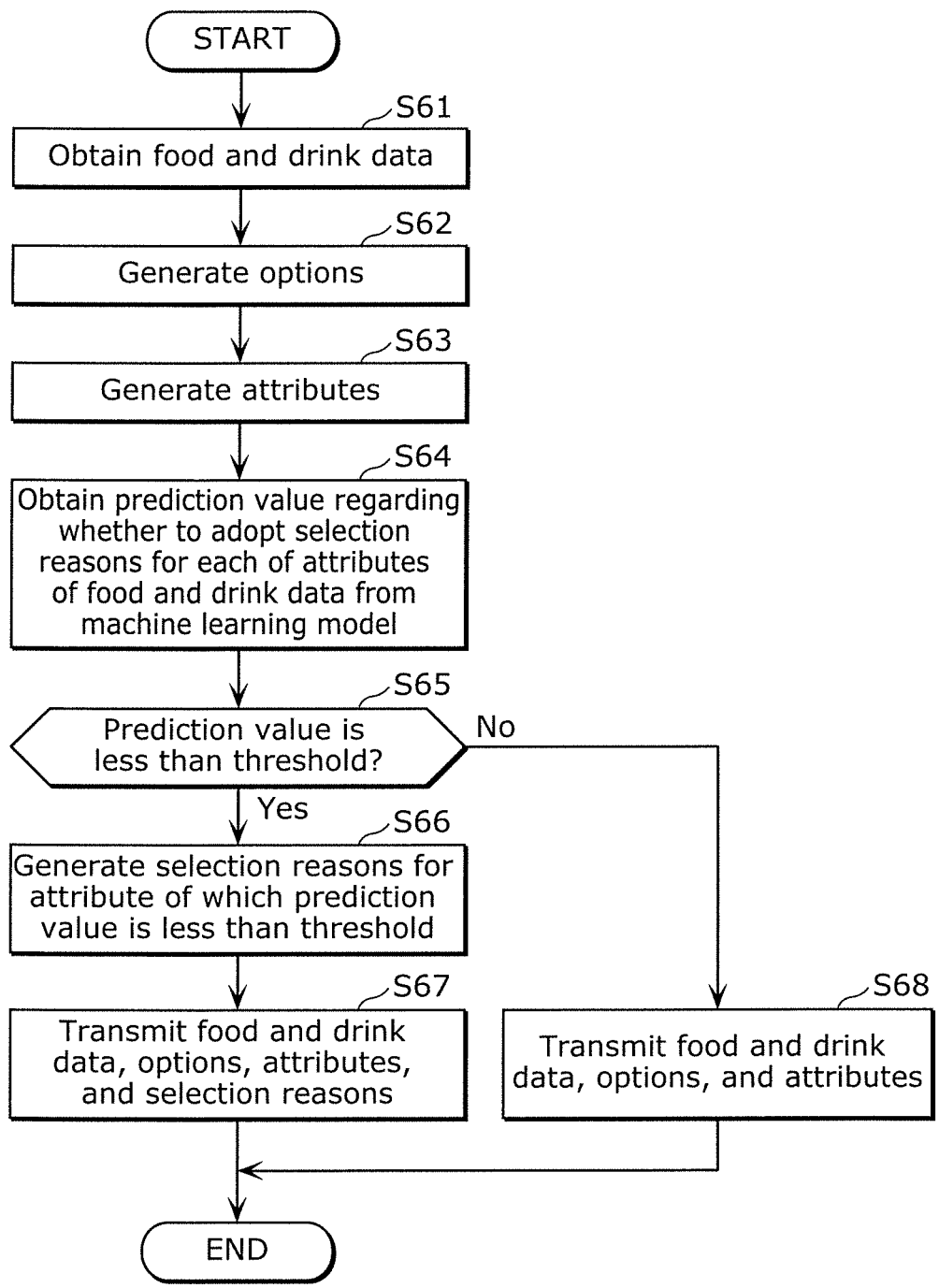

FIG. 6B is a flowchart illustrating another example of the operation of server 100 according to the variation of the embodiment when server 100 transmits the food and drink data and the like.

Content proposer 110 obtains the food and drink data from storage 130 (Step S61), generates options for the food and drink data that have been obtained (Step S62), and generates attributes of the food and drink data (Step S63).

Next, content proposer 110 obtains a prediction value regarding whether to adopt the selection reasons for each of the attributes of the food and drink data that has been output from the machine learning model (Step S64). For example, as a result of the training, when the probability that the user adopts a specific selection reason for a certain attribute of the food and drink data that has been input to the machine learning model is predicted to be high, the prediction value of the certain attribute increases. On the other hand, when it is not clear which selection reason the user adopts for a certain attribute of the food and drink data that has been input to the machine learning model, the prediction value decreases.

Next, content proposer 110 determines whether or not the obtained prediction value is less than a threshold (Step S65).

When the obtained prediction value is less than the threshold (Yes in Step S65), content proposer 110 generates selection reasons for an attribute of which the prediction value is less than the threshold (Step S66). This is because, since it is not clear which selection reason the user adopts for the attribute of which the prediction value is less than the threshold, it is necessary to present selection reasons corresponding to the attribute on presentation device 200 to cause the user to select and input a selection reason, and to further perform the training of the machine learning model for the attribute of which the prediction value is less than the threshold by using an input result.

Then, communication section 140 transmits the food and drink data, the options, attributes, and the selection reasons corresponding to the attributes to presentation device 200 (Step S67).

When the obtained prediction value is greater than or equal to the threshold, content proposer 110 does not generate selection reasons for the attribute of which the prediction value is greater than or equal to the threshold, and communication section 140 transmits the food and drink data, the options, and the attributes to presentation device 200 (Step S68). In other words, content proposer 110 does not present the selection reasons for the attribute of which the prediction value is greater than or equal to the threshold. This is because, since it is clear which selection reason the user adopts as to the attribute of which the prediction value is greater than or equal to the threshold, it is not necessary to present the selection reasons for the attribute on presentation device 200 to cause the user to select and input a selection reason, and to further perform the training of the machine learning model for the attribute of which the prediction value is greater than or equal to the threshold. As described above, for the attribute of which the prediction value regarding whether to adopt the selection reason is greater than or equal to the threshold, the training is advanced regarding which selection reason is to be selected for the attribute, and it is possible not to present selection reasons for such attribute. In other words, it is possible to prevent the user from having to be bothered to input a selection reason.

Figure 7:
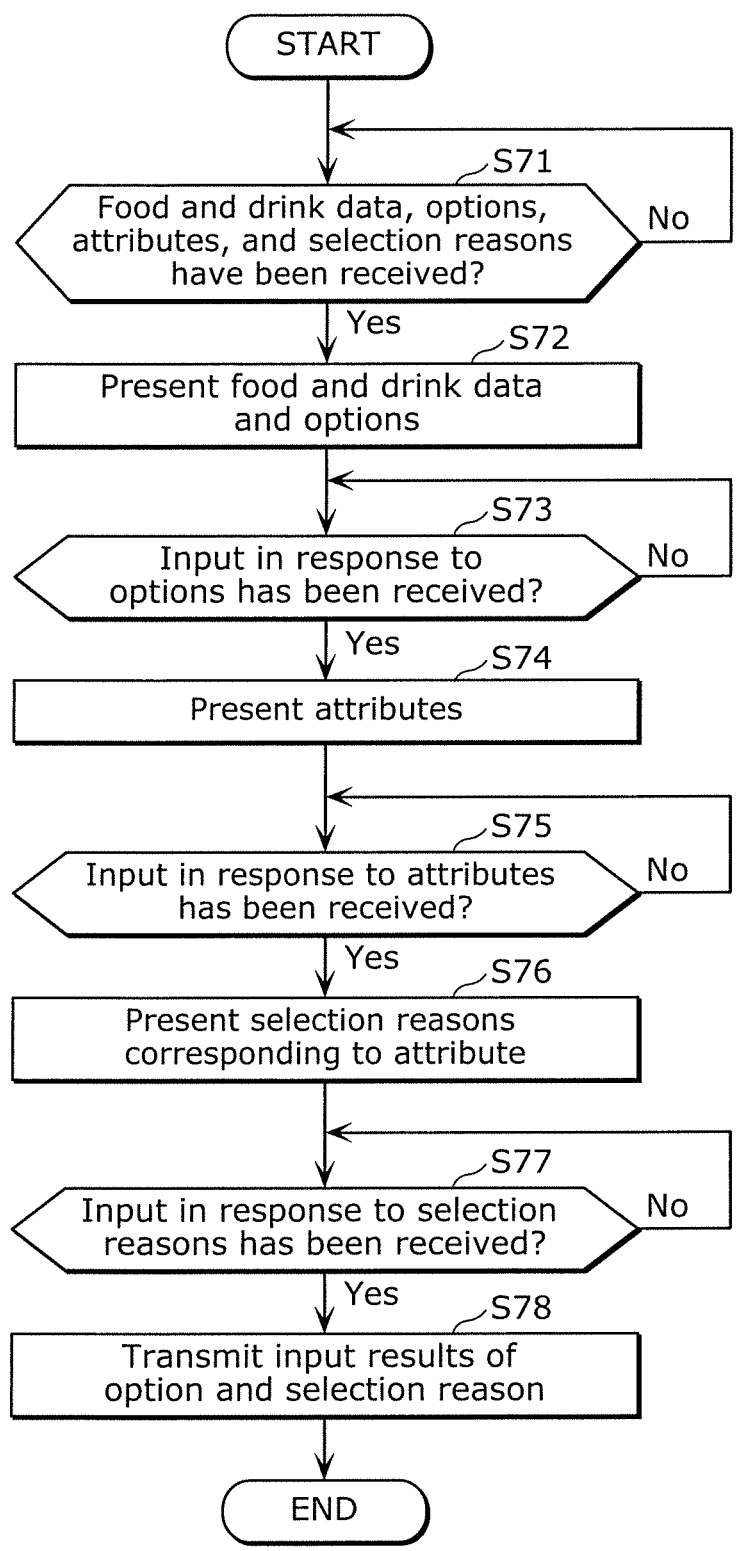
FIG. 7 is a flowchart illustrating one example of the operation performed by a presentation device according to the variation of the embodiment.

FIG. 7 is a flowchart illustrating one example of the operation performed by presentation device 200 according to the variation of the embodiment.

Presentation controller 210 determines whether communication section 240 has received the food and drink data, the options, the attributes, and the selection reasons from server 100 (Step S71). More specifically, presentation controller 210 determines whether or not communication section 240 has received UI data that includes the food and drink data, the options, the attributes, and the selection reasons from server 100.

When presentation controller 210 determines that communication section 240 has not received the food and drink data, the options, the attributes, and the selection reasons from server 100 (No in Step S71), the process in Step S71 is repeatedly performed until communication section 240 receives the food and drink data, the options, the attributes and the selection reasons.

When presentation controller 210 determines that communication section 240 has received the food and drink data, the options, the attributes, and the selection reasons from server 100 (Yes in Step S71), presentation controller 210 presents the food and drink data and the options on presentation section 220 (Step S72). More specifically, presentation controller 210 generates an image of the food and drink data and an image of the options using the UI data that includes the food and drink data, the options, the attributes, and the selection reasons, and presents these images on presentation section 220.

Next, presentation controller 210 determines whether an input in response to the options presented on presentation section 220 has been received (Step S73). More specifically, presentation controller 210 determines whether or not a user operation in response to the options presented on presentation section 220 has been received via inputting section 230.

When an input in response to the options presented on presentation section 220 has not been received (No in Step S73), presentation controller 210 repeatedly performs the process in Step S73 until an input in response to the options presented on presentation section 220 is received.

When an input in response to the options presented on presentation section 220 has been received (Yes in Step S73), presentation controller 210 presents the attributes of the food and drink data (Step S74). More specifically, presentation controller 210 generates an image of the attributes of the food and drink data, using the UI data that includes the food and drink data, the options, the attributes, and the selection reasons, and presents the image on presentation section 220.

Next, presentation controller 210 determines whether an input in response to the attributes presented on presentation section 220 has been received (Step S75). More specifically, presentation controller 210 determines whether a user operation in response to the attributes presented on presentation section 220 has been received via inputting section 230.

When an input in response to the attributes presented on presentation section 220 has not been received (No in Step S75), presentation controller 210 repeatedly performs the process in Step S75 until an input in response to the attributes presented on presentation section 220 is received.

When an input in response to the attributes presented on presentation section 220 has been received (Yes in Step S75), presentation controller 210 presents the selection reasons which correspond to the attribute selected by the input (Step S76). More specifically, presentation controller 210 generates an image of the selection reasons which correspond to the attribute, using the UI data that includes the food and drink data, the options, the attributes, and the selection reasons, and presents the image of the selection reasons on presentation section 220.

Here, the image of the food and drink data and the image of the options presented on presentation section 220, the image of the attributes presented when an input in response to the presented options has been received, and the image of the selection reasons presented when an input in response to the presented attributes has been received will be described with reference to FIG. 8.

Figure 8:
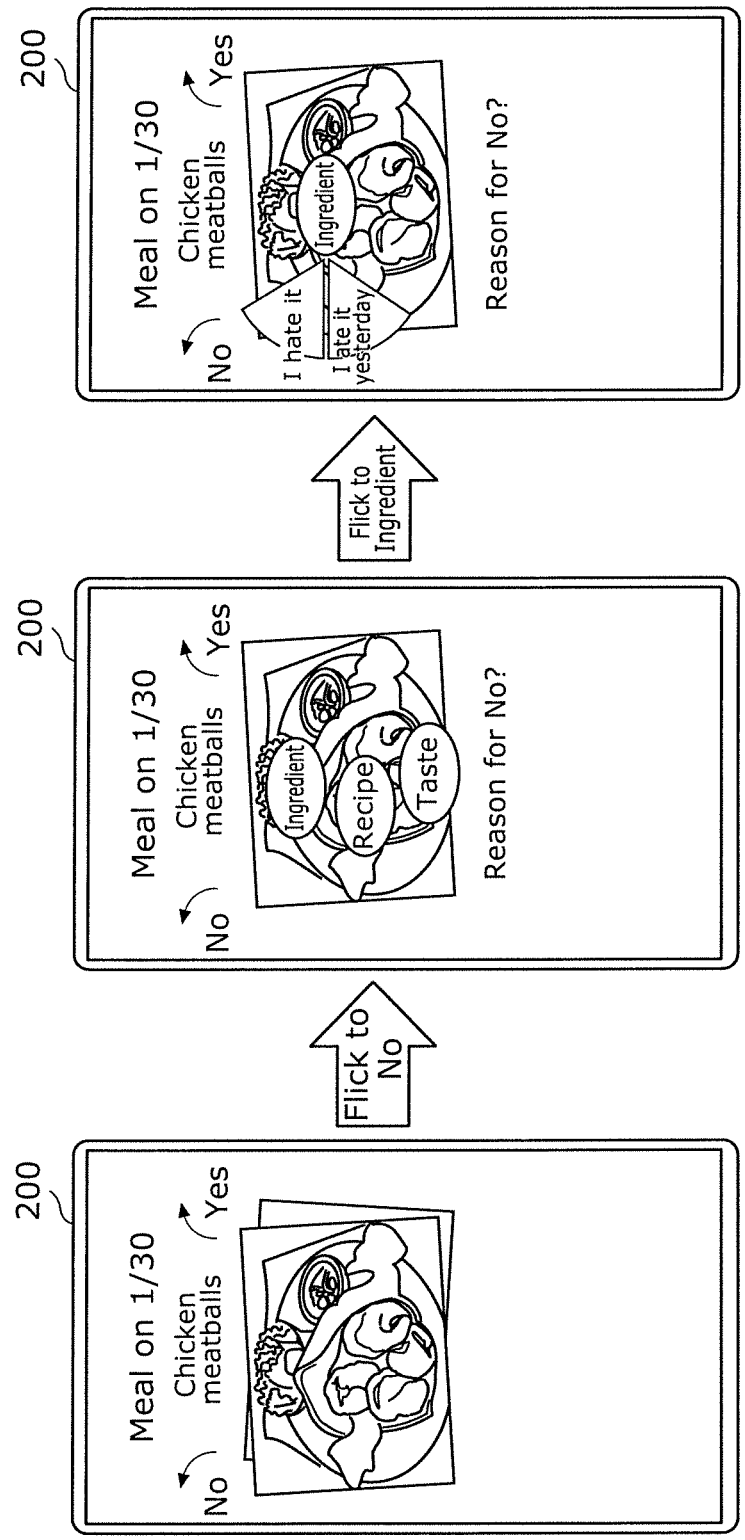
FIG. 8 is a diagram illustrating one example of images presented on the presentation device according to the variation of the embodiment.

FIG. 8 is a diagram illustrating one example of the images presented on presentation device 200 according to the variation of the embodiment. On the left side of FIG. 8, an image of the food and drink data and an image of the options presented on presentation device 200 are illustrated. At the center of FIG. 8, the image of the food and drink data, the image of the options, and an image of the attributes presented on presentation device 200 are illustrated. On the right side of FIG. 8, the image of the food and drink data, the image of the options, the image of the attribute, and an image of the selection reasons presented on presentation device 200 are illustrated.

As illustrated on the left side of FIG. 8, in the process in Step S72, an image of chicken meatballs, for example, is presented as an image of the food and drink data on presentation device 200, and an image including an option image "Yes" and an option image "No", for example, is presented as an image of the options on presentation device 200. In addition, an image of an arrow prompting a flick input toward the side on which "Yes" is presented on the screen is presented in proximity to the option image "Yes", and an image of an arrow prompting a flick input toward the side on which "No" is presented on the screen is presented in proximity to the option image "No". A user who has viewed these images performs a flick input toward the side on which the option image "Yes" is presented when adopting the chicken meatballs for a meal. When the user does not adopt the chicken meatballs for the meal, the user performs a flick input toward the side on which the option image "No" is presented. In the above-described manner, the user can perform an input in response to the options.

For example, it is assumed that the user has performed a flick input toward the side on which the option image "No" is presented. In this case, as illustrated at the center of FIG. 8, an image of attributes of the food and drink which indicates the reasons for selecting "No" is presented as an image of the attributes. Here, an image including attribute images "Ingredient", "Recipe", and "Taste" are presented as an image of the attributes. When the reason for not adopting chicken meatballs for the meal is the ingredient (for example, chicken), the user performs a flick input toward the attribute image "Ingredient". When the reason for not adopting chicken meatballs for the meal is the recipe (for example, deep flying), the user performs a flick input toward the attribute image "Recipe". When the reason for not adopting chicken meatballs for the meal is the seasonings (for example, salt), the user performs a flick input toward the attribute image "Taste". In the above-described manner, the user can perform an input in response to the attributes.

For example, it is assumed that the user has performed, as an input in response to the attributes, a flick input toward the side on which the attribute image "Ingredient" is presented. In this case, as illustrated on the right side of FIG. 8, on the side on which "No" is presented in the screen, as selection reason images that correspond to the attribute, an image of reasons for not adopting the chicken meatballs for the meal when the ingredient is focused for the reason why chicken meatballs are not adopted for the meal is presented as an image of the reason. Here, selection reason images "I hate it" and "I ate it yesterday" are presented as the selection reason images corresponding to the attribute "Ingredient". When the reason for not adopting the chicken meatballs for the meal is that the user hates chicken, the user performs a flick input toward the selection reason image "I hate it". When the reason for not adopting the chicken meatballs for the meal is that the user ate chicken meatballs yesterday, the user performs a flick input toward the selection reason image "I ate it yesterday". In the above-described manner, the user can perform an input of the selection reason corresponding to the attribute.

It should be noted that, although the case where an input of the selection reason is performed by selecting one selection reason from among specific selection reasons such as "I hate it" and "I ate it yesterday", the present disclosure is not limited to this example. For example, the degree of the selection reason may be input. This will be described with reference to FIG. 9.

Figure 9:
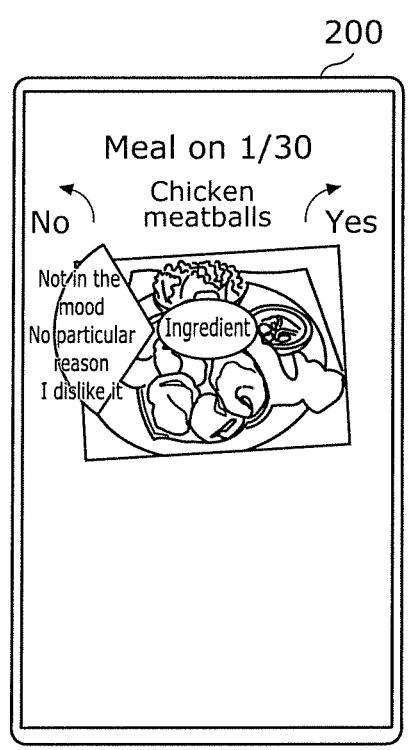
FIG. 9 is a diagram illustrating another example of the images presented on the presentation device according to the variation of the embodiment.

FIG. 9 is a diagram illustrating another example of the images presented on presentation device 200 according to the variation of the embodiment. In FIG. 9, an image of the selection reasons when an input in response to the attributes has been received.

In FIG. 9, an image including selection reason images "Not in the mood", "No particular reason", and "I dislike it" is illustrated as an image of the selection reasons, which is a single image that includes no boundary. In a region of this integrated image, "Not in the mood" is presented on the upper side, "No particular reason" is presented at the center, and "I dislike it" is presented on the lower side. When the upper side of the region is selected, the degree of preference for the ingredient indicates a tendency of liking the ingredient. When the lower side of the region is selected, the degree of preference for the ingredient indicates a tendency of disliking the ingredient. The degree of the selection reason may be input in the above-described manner.

In addition, in this case, a parameter with which the effect of the training decreases as the selection reason is more ambiguous may be determined. For example, when the selection reason that has been selected is "No particular reason", trainer 120 trains the model in such a way that the food and drink data "chicken meatballs" is less likely to be proposed as a meal candidate, with a parameter with which the effect of the training is reduced. Alternatively, when the selection reason is ambiguous, the training need not be carried out.

Returning back to the description of FIG. 7, presentation controller 210 determines whether an input regarding the selection reasons presented on presentation section 220 has been received (Step S77). More specifically, presentation controller 210 determines whether a user operation regarding the selection reasons presented on presentation section 220 has been received via inputting section 230.

When an input for the selection reasons presented on presentation section 220 has not been received (No in Step S77), presentation controller 210 repeats the process in Step S77 until an input for the selection reasons presented on presentation section 220 is received.

In the case where an input for the selection reasons presented on presentation section 220 has been received (Yes in Step S77), presentation controller 210 transmits input results in response to the options and the selection reasons via communication section 240 to server 100 (Step S78). For example, when the user does not adopt chicken meatballs for the meal and the reason therefor is that the user hates the ingredient (chicken), the input result in response to the options indicates that the chicken meatballs are not adopted, and the input result in response to the selection reasons indicates that the reason for not adopting chicken meatballs is that the user hates chicken.

It should be noted that, when the selection reason is not received in Step S71, that is, when food and drink data, options, and attributes are transmitted and selection reasons are not transmitted from server 100 as in Step S68 in FIG. 6B, the processes of Step S76 and Step S77 need not be performed, and an input result in response to the selection reasons need not be transmitted in Step S78.

Figure 10:
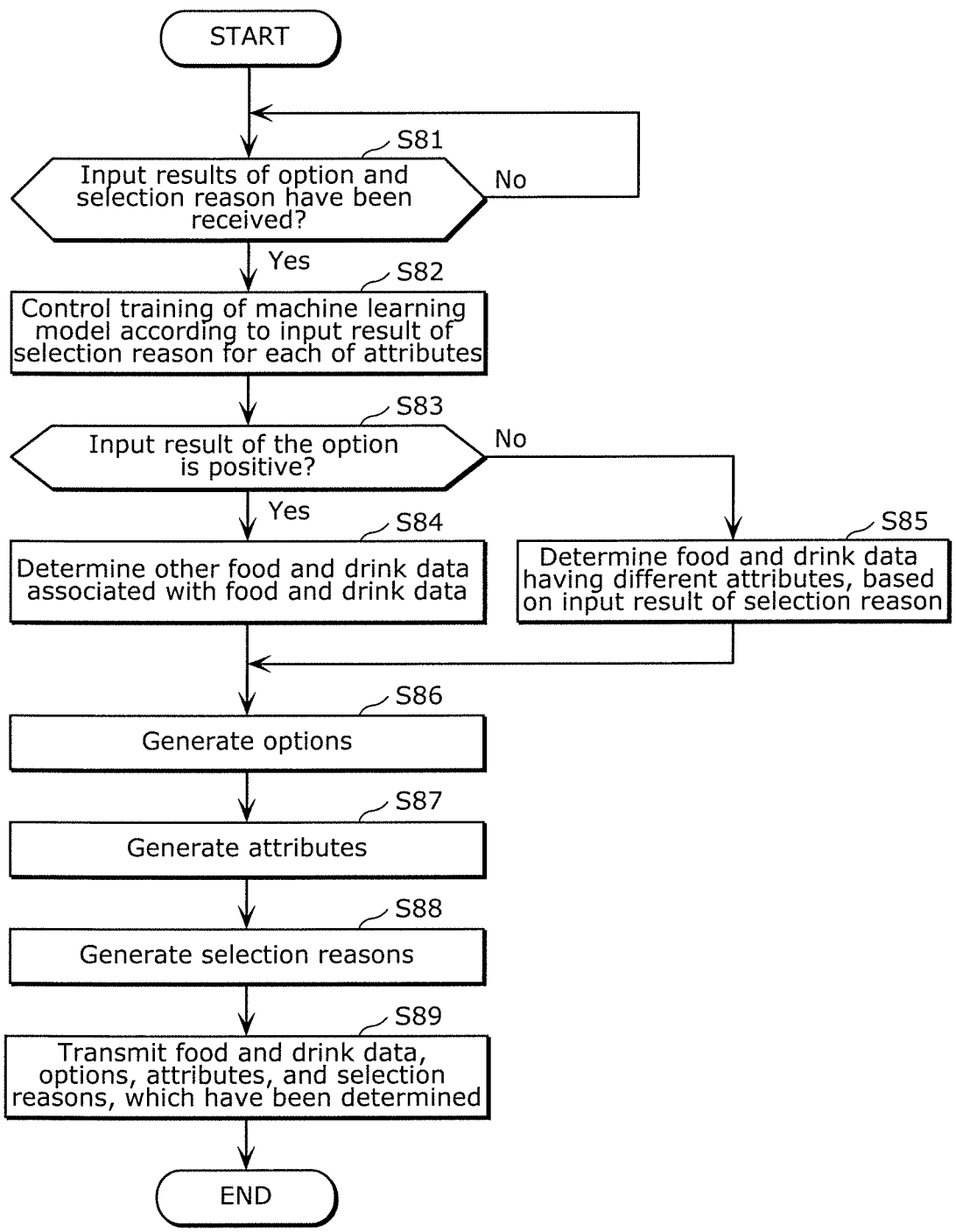
FIG. 10 is a flowchart illustrating one example of the operation performed by the server according to variation of the embodiment when the server receives an input result.

FIG. 10 is a flowchart illustrating one example of the operation of server 100 according to the variation of the embodiment when server 100 receives an input result.

Trainer 120 determines whether communication section 140 has received input results in response to the options and the selection reasons from presentation device 200 (Step S81).

When trainer 120 determines that communication section 140 has not received input results in response to the options and the selection reasons from presentation device 200 (No in Step S81), communication section 140 repeats the process in Step S81 until communication section 140 receives the input results in response to the options and the selection reasons.

When trainer 120 determines that communication section 140 has received input results in response to the options and the selection reasons from presentation device 200 (Yes in Step S81), trainer 120 controls a training of a machine learning model, in which the food and drink data is used, according to the input result in response to the selection reasons for each of the attributes (Step S82).

For example, trainer 120 may determine a parameter for the training according to the input result in response to the selection reasons for each of the attributes, and train the machine learning model with the parameter that has been determined. In addition, for example, trainer 120 may determine whether or not to perform the training according to the input result in response to the selection reasons for each of the attributes. For example, when the attribute that has been selected is the ingredient and the selection reason that has been selected is "I hate it", trainer 120 trains the model in such a way that the food and drink data "chicken meatballs" and the ingredient "chicken" are less likely to be proposed as meal candidates, with a parameter with which the effect of the training is increased. In other words, the machine learning model is trained using the food and drink data and the attribute as the training data.

Next, trainer 120 determines whether or not the input result in response to the options is positive (Step S83).

When the input result in response to the options is positive (Yes in Step S83), content proposer 110 determines other food and drink data that is associated with the food and drink data (Step S84).

On the other hand, when the input result in response to the options is negative (No in Step S83), content proposer 110 determines food and drink data having different attributes, based on the input result in response to the selection reasons (Step S85). The food and drink data having different attributes is food and drink data that does not apply to the selection reason corresponding to the attribute for not adopting the presented food and drink data. For example, when the presented food and drink data indicates chicken meatballs that are the main dish, and the selection reason for not adopting it indicates that the user ate chicken yesterday, the next food and drink data is food and drink data that is different from the food and drink data indicating use of chicken; that is, food and drink data indicating no use of chicken, and that can be a main dish. In this manner, when the input result in response to the options for the presented food and drink data is negative, it is possible to present food and drink data that differs in attributes (for example, food and drink data that differs in the ingredient, the recipe, the seasonings, or the like).

Then, content proposer 110 generates options additionally for the food and drink data that has been determined (Step S86), generates attributes (Step S87), and generates selection reasons that correspond to the attributes (Step S88), and communication section 140 transmits the food and drink data that has been determined, the options, the attributes, and the selection reasons, to presentation device 200 (Step S89). As a result, content proposer 110 additionally presents the food and drink data that has been determined via presentation device 200, and the processes illustrated in FIG. 6A, FIG. 6B, FIG. 7, and FIG. 10 are performed.

It should be noted that, when some items of the food and drink data are adopted and all the meal components are determined, the processing may be ended without performing the processes of Step S83 and the processes subsequent to Step S83.

In addition, when an input result in response to the selection reasons is not received in Step S81, that is, when food and drink data, options, and attributes are transmitted and selection reasons are not transmitted from server 100 as in Step S68 in FIG. 6B, and an input result in response to the selection reasons is not transmitted in Step S788 in FIG. 7, the processes of Step S82 need not be performed.

It should be noted that, it is not necessary to repeat, for each items of food and drink data, presenting once the food and drink data, the options, the attributes, and the selection reasons, and controlling the training of the machine learning model according to the input results. More specifically, a plurality of items of food and drink data and the respective options, attributes, and selection reasons of the plurality of items of food and drink data may be collectively transmitted to presentation device 200. In this case, presentation device 200 may repeat the processes from Step S72 to Step S77 in FIG. 7 for each of the plurality of items of food and drink data which have been received, and input results in response to the respective options and selection reasons of the plurality of items of food and drink data may be collectively transmitted to server 100. Then, the training of the machine learning model may be controlled according to the input results of the respective options and selection reasons of the plurality of items of food and drink data.

As described above, the selection reason for the options for the food and drink data includes various reasons for each of the attributes such as an ingredient, recipe, seasonings, or the like of the food and drink data. Accordingly, it is possible to efficiently perform training of a machine learning model, by generating and presenting selection reasons that correspond to attributes and controlling the training of the machine learning model according to the input result in response to the selection reasons for each of the attributes.

Other Embodiments

Although the information processing method and server 100 (information processing system) according to one or more aspects of the present disclosure have been described above based on the embodiment, the present disclosure is not limited to the above-described embodiment. Other forms in which various modifications apparent to those skilled in the art are applied to the embodiments, or forms structured by combining structural components of different embodiments may be included within the scope of one or more aspects of the present disclosure, unless such changes and modifications depart from the scope of the present disclosure.

For example, a sound obtained during a flick input may be obtained as an input result in response to the selection reasons. For example, a sound input function of presentation device 200 may be activated from the start of a flick input till the end of the flick input, a sound made by user's utterance may be collected during the period, and a result of recognizing the sound may be an input result of a selection reason.

In addition, for example, as described with reference to FIG. 9, in the case where, when the degree of a selection reason is input, although "Yes" is selected as an option, the selection reason is "No particular reason", "I dislike it", or the like, the selection of "Yes" is not positively made. Accordingly, detailed options for asking the user what a dissatisfying point is may be generated, and the user may be caused to input the dissatisfying point. Then an input result of the dissatisfying point may be used for the learning. In addition, when the degree of a selection reason is input, for example, in the case where "No" is selected as an option and "I hate it" is the selection reason, the learning may be carried out with emphasis on that the selected option is "No".

In addition, for example, inputting an option and a selection reason is not limited to the flick input, and may be carried out by tap input, swipe input, etc.

In addition, for example, presenting the selection reasons may be controlled according to a speed or a strength of an input of an option. For example, when an input in response to the options is made with a high speed or a high strength, it is highly likely that the user has input the option judging by the appearance of an image of the presented food and drink data. In view of this, selection reasons that are related to appearances may be presented. In addition, for example, when an input in response to the options is made with a low speed or a low strength, there is a possibility that the user is wavering over the selection of the presented food and drink data for some reason. In view of this, other detailed selection reasons may be presented.

In addition, for example, the selection reasons may be generated based on the features of the food and drink data, including an image of the food and drink, a dish name of the food and drink, etc. For example, a color feature of food and drink data may be extracted from the image of the food and drink data, and selection reasons may be generated based on the color feature. More specifically, when green color is not contained in the image, a selection reason "vegetable is not sufficient" may be generated. In addition, for example, a feature of attributes of food and drink data may be extracted from the dish name of the food and drink data, and selection reasons may be generated based on the feature of attributes. More specifically, when the dish name is "Pork and bean sprout stir-fries", selection reasons "Pork", "Bean sprout", and "Stir-fries" may be generated. In addition, when a tag "time shortening" is associated with the food and drink data, a selection reason "Time shortening" may be generated.

In addition, for example, regarding the above-described case where a positive or a negative option for the meal is presented, an option that is positive or negative to a recipe, eating-out, home-meal replacement, etc. may be presented.

In addition, for example, regarding the above-described case where training is controlled according to an input result in response to selection reasons or options, information processing system 100 may sort out data for training according to the input result in response to the selection reasons or the options.

For example, with reference to the example of FIG. 4, when the selection reason that has been selected is "I hate it", trainer 120 classifies the food and drink data "chicken meatballs" as data to be trained with a parameter with which an effect of the training is increased, in such a way that the food and drink data "chicken meatballs" is less likely to be proposed as a meal candidate. In addition, for example, when the selection reason that has been selected is "I ate it yesterday", trainer 120 classifies the food and drink data "chicken meatballs" as data to be trained in such a way that the food and drink data "chicken meatballs" is less likely to be proposed as a meal candidate, but with a parameter with which an effect of the training is reduced. Alternatively, in the latter case, the food and drink data may be determined as data not to be trained.

In addition, for example, with reference to the example of FIG. 8, when the selection reason that has been selected is "I hate it", trainer 120 classifies a combination of the food and drink data "chicken meatballs" and the ingredient "chicken" as data to be trained in such a way that combination of the food and drink data "chicken meatballs" and the ingredient "chicken" is less likely to be proposed as a meal candidate, with a parameter with which an effect of the training is increased.

In addition, for example, with reference to the example of FIG. 9, when the selection reason that has been selected is "No particular reason", trainer 120 trains the model in such a way that the food and drink data "chicken meatballs" and the ingredient "chicken" are less likely to be proposed as a meal candidate, with a parameter with which the effect of the training is reduced. Alternatively, the combination of the food and drink data and the ingredient may be determined as data not to be trained.

The present disclosure can be implemented as a program for causing a processor to execute the steps included in the information processing method. In addition, the present disclosure can be implemented as a non-transitory computer-readable recording medium such as a compact disc-read only memory (CD-ROM) including the program recorded thereon.

For example, when the present disclosure is implemented by a program (software), each of the steps is performed as a result of the program being executed by utilizing hardware resources such as a CPU, a memory, an input and output circuit, etc. of a computer. More specifically, the CPU obtains data from a memory, an input and output circuit, or the like, and calculates the obtained data, or outputs a result of calculation to the memory or the input and output circuit, or the like. As a result, each of the steps is performed.

It should be noted that, in the above-described embodiment, each of the structural components included in server 100 may be configured in the form of a dedicated hardware product, or may be realized by executing a software program suitable for the structural components. Each of the structural components may be realized by means of a program executing unit, such as a central processing unit (CPU) and a processor, reading and executing the software program recorded on a recording medium such as a hard disk or a semiconductor memory.

In addition, all or part of the functions of server 100 according to the foregoing embodiment is implemented typically as an LSI that is an integrated circuit. They may be realized as a single chip one-by-one, or as a single chip to include part or all of them. In addition, the integrated circuit is not limited to an LSI, and it may be implemented as a dedicated circuit or a general-purpose processor. Field Programmable Gate Array (FPGA) that can be programmed after manufacturing LSIs or a reconfigurable processor that allows re-configuration of the connection or settings of circuit cells inside an LSI may be used for the same purpose.

Furthermore, other forms in which various modifications apparent to those skilled in the art are applied to the embodiments of the present disclosure may be included within the scope of one or more aspects of the present disclosure, unless such changes and modifications depart from the scope of the present disclosure.

Each of the elements in each of the above-described embodiments may be configured in the form of an exclusive hardware product, or may be realized by executing a software program suitable for the element. Each of the elements may be realized by means of a program executing unit, such as a CPU and a processor, reading and executing the software program recorded on a recording medium such as a hard disk or a semiconductor memory. Here, the software program for realizing XXX apparatus according to each of the embodiments is a program described below.

The herein disclosed subject matter is to be considered descriptive and illustrative only, and the appended Claims are of a scope intended to cover and encompass not only the particular embodiments disclosed, but also equivalent structures, methods, and/or uses.

INDUSTRIAL APPLICABILITY

The information processing method, etc. according to the present disclosure are applicable to a device that learns user's preferences in regard to food and drink, for example.

The invention claimed is:

1. An information processing method executed by a computer, the information processing method comprising:
   obtaining food and drink data and presenting the food and drink data via a presentation device;
   generating options for the food and drink data, and presenting the options via the presentation device;
   generating selection reasons according to an option selected from among the options, and presenting the selection reasons via the presentation device; and
   controlling training of a machine learning model according to a result of an input in response to the selection reasons, the training using the food and drink data,
   wherein
   (i) the result of the input in response to the selection reasons includes at least one of a direction, a strength, or a speed of the input in response to the selection reasons; or (ii) a result of an input in response to the options includes at least one of a direction, a strength, or a speed of the input in response to the options,
   in the presenting of the selection reasons, the presenting of the selection reasons is controlled according to at least one of the speed or the strength of the input in response to the options, and
   the controlling of the training includes:
   determining a parameter for the training according to the result of the input in response to the selection reasons; and
   controlling the training using the parameter.

2. The information processing method according to claim 1, wherein
   the parameter is a weighting parameter of the food and drink data.

3. The information processing method according to claim 1, wherein
   the parameter is a reward in reinforcement learning.

4. The information processing method according to claim 1, wherein
   in the determining of the parameter,
   the parameter for the training is determined additionally according to a result of an input in response to the options.

5. The information processing method according to claim 1, wherein
   in the determining of the parameter,
   when the input in response to the selection reasons is not immediately made, the parameter determined is a parameter with which an effect of the training is reduced.

6. The information processing method according to claim 1, wherein
   in the determining of the parameter,
   when the input in response to the selection reasons is immediately made, the parameter determined is a parameter with which an effect of the training is increased.

7. The information processing method according to claim 1, wherein
   in the controlling of the training,
   whether to perform the training is determined according to the result of the input in response to the selection reasons.

8. The information processing method according to claim 1, wherein
   the machine learning model outputs a prediction value regarding selection from among the options for the food and drink data, the prediction value being obtained by inputting the food and drink data into the machine learning model,
   the prediction value is obtained from the machine learning model, and
   the information processing method further comprising presenting, after the machine learning model outputs the prediction value, only the selection reasons for the food and drink data of which the prediction value is less than a threshold.

9. The information processing method according to claim 1, wherein
   when the result of the input in response to the options is positive, other food and drink data associated with the food and drink data is presented via the presentation device.

10. The information processing method according to claim 1, wherein
    when the result of the input in response to the options is negative, next food and drink data is determined based on the result of the input in response to the selection reasons, and presented via the presentation device.

11. The information processing method according to claim 1, wherein
    the selection reasons are generated based on a feature of the food and drink data.

12. The information processing method according to claim 1, wherein
    an input in response to the options and the input in response to the selection reasons are made by flick input.

13. The information processing method according to claim 12, wherein
    a sound obtained during the flick input is obtained as the result of the input in response to the selection reasons.

14. An information processing method executed by a computer, the information processing method comprising:
    obtaining food and drink data and presenting the food and drink data via a presentation device;
    generating options for the food and drink data, and presenting the options via the presentation device;
    generating attributes of the food and drink data according to an option selected from among the options, and presenting the attributes via the presentation device;
    generating selection reasons according to an attribute selected from among the attributes of the food and drink data, and presenting the selection reasons via the presentation device; and
    controlling training of a machine learning model according to a result of an input in response to the selection reasons, the training using the food and drink data,
    wherein
    in the presenting of the selection reasons, the selection reasons corresponding to the attribute selected are generated and presented via the presentation device,
    the machine learning model outputs a prediction value regarding whether to adopt the selection reasons for each of the attributes of the food and drink data, the prediction value being obtained by inputting the food and drink data into the machine learning model,
    the prediction value is obtained from the machine learning model, and the selection reasons for the attribute of which the prediction value is greater than or equal to the threshold is not presented.

15. The information processing method according to claim 14, wherein when the result of the input in response to the options is negative, the food and drink data of which the attributes are different is determined based on the result of the input in response to the selection reasons, and presented via the presentation device.

16. An information processing system, comprising:

a processor; and memory in which a program is stored, wherein when the program is executed by the processor, the program causes the processor to perform:
  obtaining food and drink data;
  generating options for the food and drink data;
  generating selection reasons corresponding to an option selected from among the options;
  presenting the food and drink data, the options, and the selection reasons, via a presentation device; and
  controlling training of a machine learning model according to a result of an input in response to the selection reasons, the training using the food and drink data, (i) the result of the input in response to the selection reasons includes at least one of a direction, a strength, or a speed of the input in response to the selection reasons; or (ii) a result of an input in response to the options includes at least one of a direction, a strength, or a speed of the input in response to the options, in the presenting of the selection reasons, the processor is caused to perform controlling of the presenting of the selection reasons according to at least one of the speed or the strength of the input in response to the options, and the controlling of the training includes causing the processor to perform:
  determining a parameter for the training according to the result of the input in response to the selection reasons; and
  controlling the training using the parameter.

17. An information processing system, comprising:

a processor; and memory in which a program is stored, wherein when the program is executed by the processor, the program causes the processor to perform:
  obtaining food and drink data and presenting the food and drink data via a presentation device;
  generating options for the food and drink data, and presenting the options via the presentation device;
  generating attributes of the food and drink data according to an option selected from among the options, and presenting the attributes via the presentation device;
  generating selection reasons according to an attribute selected from among the attributes of the food and drink data, and presenting the selection reasons via the presentation device; and
  controlling training of a machine learning model according to a result of an input in response to the selection reasons, the training using the food and drink data, in the presenting of the selection reasons, the selection reasons corresponding to the attribute selected are generated and presented via the presentation device, and the program further causes the processor to perform processing in which:
  the machine learning model outputs a prediction value regarding whether to adopt the selection reasons for each of the attributes of the food and drink data, the prediction value being obtained by inputting the food and drink data into the machine learning model;
  the prediction value is obtained from the machine learning model; and
  the selection reasons for the attribute of which the prediction value is greater than or equal to the threshold is not presented.

* * * * *